(12) United States Patent
Waldner et al.

(10) Patent No.: US 9,061,303 B2
(45) Date of Patent: Jun. 23, 2015

(54) INHALATION THERAPY DEVICE

(75) Inventors: Robert Waldner, Peiting (DE); Daniela Mundenbruch, München (DE); Uwe Hetzer, München (DE); Markus Urich, München (DE)

(73) Assignee: Pari Pharma GmbH, Starnberg (DE)

( * ) Notice: Subject to any disclaimer, the term of this patent is extended or adjusted under 35 U.S.C. 154(b) by 1983 days.

(21) Appl. No.: 10/538,515

(22) PCT Filed: Dec. 9, 2003

(86) PCT No.: PCT/EP03/13959
§ 371 (c)(1),
(2), (4) Date: Sep. 12, 2007

(87) PCT Pub. No.: WO2004/052436
PCT Pub. Date: Jun. 24, 2004

(65) Prior Publication Data
US 2008/0060640 A1    Mar. 13, 2008

(30) Foreign Application Priority Data
Dec. 9, 2002 (DE) .................................. 102 57 381

(51) Int. Cl.
*B05B 17/06* (2006.01)
*A61M 15/00* (2006.01)
*A61M 11/00* (2006.01)
*B05B 17/00* (2006.01)

(52) U.S. Cl.
CPC .............. *B05B 17/00* (2013.01); *B05B 17/0638* (2013.01); *B05B 17/06* (2013.01); *A61M 11/005* (2013.01); *A61M 15/0085* (2013.01); *A61M 15/0086* (2013.01); *A61M 15/0015* (2014.02)

(58) Field of Classification Search
CPC ............ A61M 15/00; A61M 15/0005; A61M 15/001; A61M 15/0013–15/002; A61M 15/0085; A61M 15/0091; A61M 11/00–11/003; A61M 11/005; A61M 11/02; A61M 11/06–11/08; B05B 17/00–17/0692; B05B 2017/00; B05B 7/00; B05B 7/0075–17/087; B05B 11/06; B05B 11/062; B05B 1/34–1/3494
USPC ............ 128/200.21, 200.24, 200.14, 200.16, 128/200.18, 203.14, 203.23, 203.12, 128/203.15, 203.16, 203.19, 203.24, 128/207.14, 207.16; 222/161, 202, 203; 239/4, 102.1, 102.2, 329, 338, 570, 239/571
See application file for complete search history.

(56) References Cited

U.S. PATENT DOCUMENTS 4,113,809 A * 9/1978 Abair et al. ...................... 261/81
5,551,416 A * 9/1996 Stimpson et al. ......... 128/200.16
5,720,280 A * 2/1998 Elstran et al. ............ 128/205.25

(Continued)

FOREIGN PATENT DOCUMENTS

| DE | 199 53 317 | 2/2001 |
|---|---|---|
| DE | 100 22 795 | 11/2001 |
| WO | WO 98/32479 | 7/1998 |

*Primary Examiner* — Rachel Young
(74) *Attorney, Agent, or Firm* — Merchant & Gould P.C.

(57) ABSTRACT

The inhalation therapy device comprises an aerosol generator (2) and a mixing chamber (3). The introduction of ambient air is achieved by means of supply channels (9) under the control of an inspiration valve (20), including an aerosol passage (22), a region with inspiration air through openings (23) and a valve element (21). The aerosol passage (22) surrounds the membrane (6) of the aerosol generator (2), whereby a front face edge of the tubular aerosol passage (22) lies along a sealing line (20*a*) on a surface of the aerosol generator (2).

17 Claims, 8 Drawing Sheets

(56) References Cited

U.S. PATENT DOCUMENTS

Figure 1:
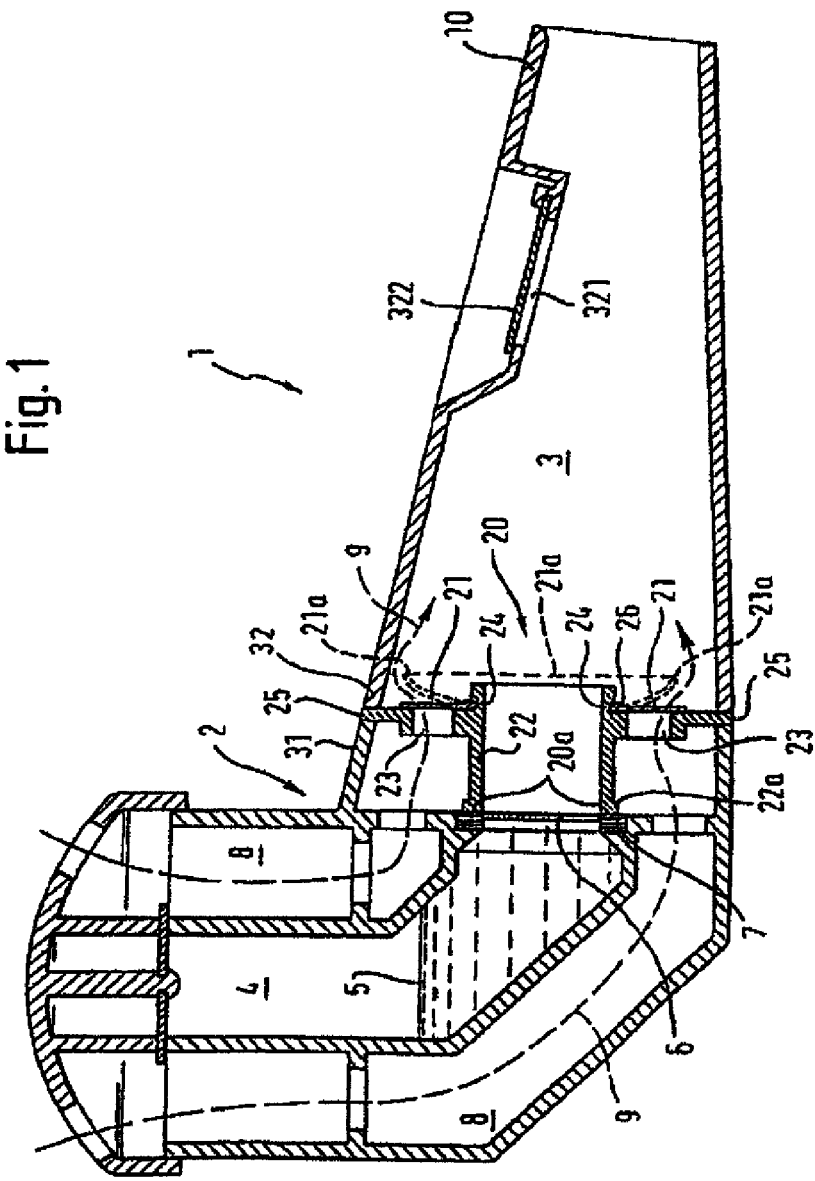

| | | | |
|---|---|---|---|
| 5,908,158 A * | 6/1999 | Cheiman | 239/102.2 |
| 6,062,212 A | 5/2000 | Davison et al. | |
| 6,176,237 B1 * | 1/2001 | Wunderlich et al. | 128/203.12 |
| 6,412,481 B1 | 7/2002 | Bienvenu et al. | |
| 6,443,146 B1 * | 9/2002 | Voges | 128/200.14 |
| 6,584,971 B1 * | 7/2003 | Denyer et al. | 128/203.14 |
| 6,851,626 B2 * | 2/2005 | Patel et al. | 239/338 |
| 7,059,320 B2 * | 6/2006 | Feiner et al. | 128/200.16 |
| 7,225,807 B2 * | 6/2007 | Papania et al. | 128/203.12 |
| 2002/0100475 A1 * | 8/2002 | McKinney et al. | 128/203.11 |

\* cited by examiner

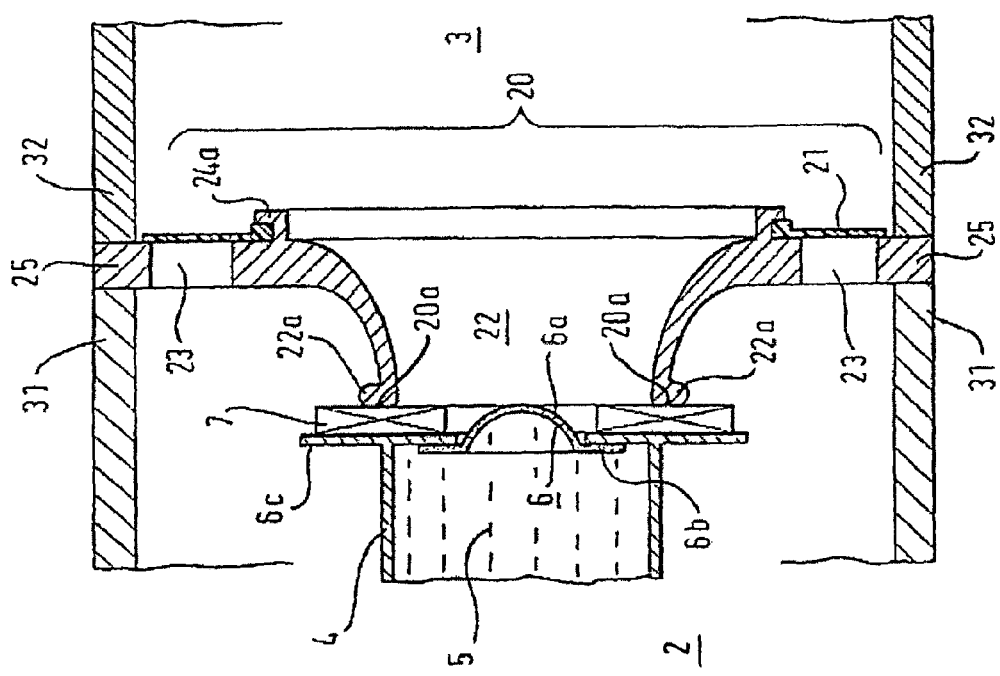

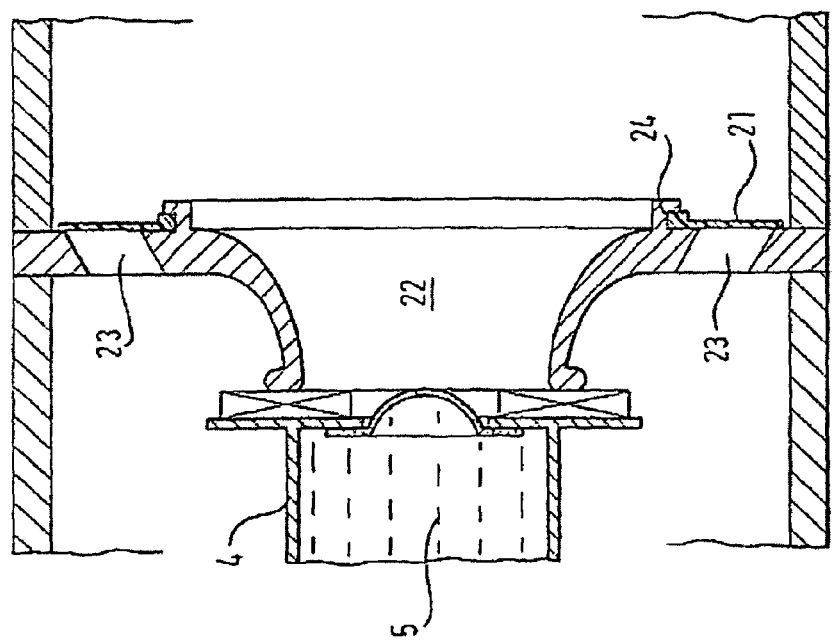

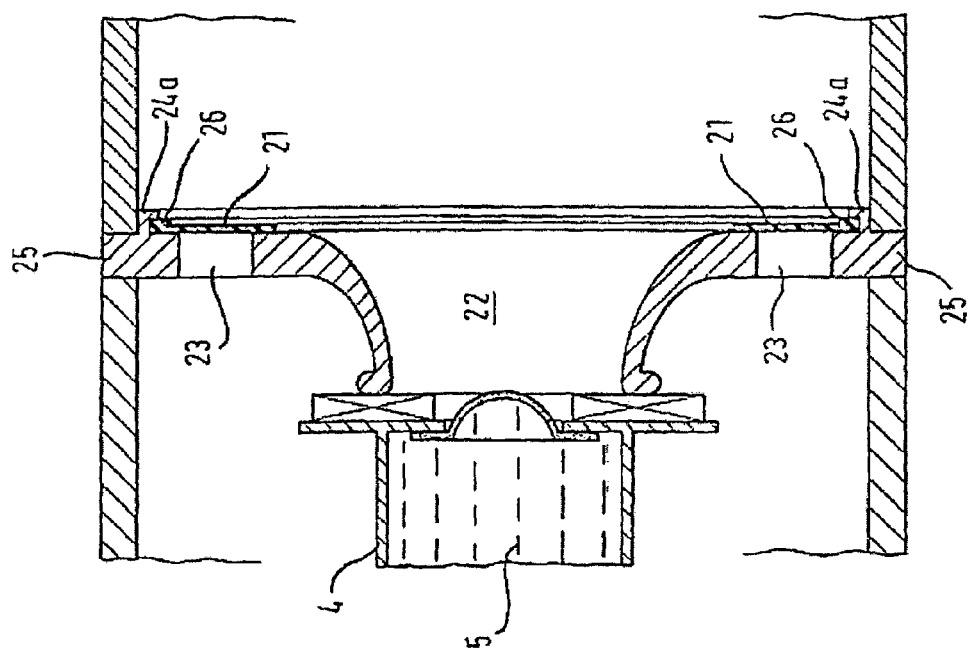

INHALATION THERAPY DEVICE

The invention relates to an inhalation therapy device having an aerosol membrane generator and a mixing chamber as well as an inhalation valve.

Liquids containing medicaments, liquid medicaments or other liquids that can be used for therapy, for example saline solutions, can be nebulised with inhalation therapy devices of this type in order to present the patient with an aerosol for inhalation.

DE 199 53 317 A describes such an inhalation therapy device having a membrane aerosol generator, the membrane of which is caused to oscillate by an oscillation generator, whereby a liquid disposed on one side of the membrane is nebulised through said membrane and is released into a mixing chamber. In the mixing chamber, the aerosol mixes with ambient air during the inhalation process, which is supplied to the mixing chamber via an annular gap that is formed around a liquid storage container. A flat, annular inhalation valve is provided in the annular gap, which opens said annular gap during the inhalation phase and closes it during the exhalation phase.

When, in the known therapy nebuliser, the patient exhales into the device, even though a large part of the exhaled air directly reaches the surrounding environment via an exhalation valve provided in a mouthpiece of the device, the aerosol membrane generator and the region of the liquid storage container are, however, also exposed to some of the exhaled air. This leads to undesirable contaminations of the aerosol generator.

Against the background of this prior art, the problem to be solved by the invention is to describe an inhalation therapy device in which the inhalation valve is designed such that the risk of contamination of the aerosol membrane generator by the air exhaled by the patient during exhalation phases is reduced.

This problem is solved according to the invention by an inhalation therapy device having an aerosol membrane generator, a liquid storage container into which a liquid that can be used for therapy is fillable, a membrane which is connected with the liquid container on one side such that a liquid disposed in the liquid storage container contacts one side of said membrane, and an oscillation generator for generating oscillations, by means of which a liquid disposed in the liquid storage container is nebulised into an aerosol through openings in the membrane to the other side of said membrane. The inhalation therapy device according to the invention furthermore comprises a mixing chamber into which the aerosol membrane generator generates the aerosol, and an inhalation valve which allows the inflow of ambient air into the mixing chamber during inhalation phases and which prevents the aerosol from escaping from the mixing chamber during exhalation phases and which forms a wall section of the mixing chamber. The inhalation valve in turn comprises an aerosol passage, via which the aerosol generated by the membrane generator arrives in the mixing chamber, said aerosol passage being disposed with one section on a surface of the aerosol membrane generator so as to surround the membrane along at least one sealing line and extending in an opening manner into the mixing chamber, at least one breathing air through opening disposed in a region around the aerosol passage, and a valve element disposed in the region around the aerosol passage such that the valve element closes the at least one breathing air through opening in exhalation phases and opens it in inhalation phases.

The spatially adjacent arrangement of the aerosol passage, the breathing air through opening and the valve element creates an inhalation valve which is suitable as a wall section of the mixing chamber and can thereby be disposed in front of the membrane nebuliser. The parts of the complete device disposed outside of the mixing chamber are therefore better protected from contamination. The aerosol passage not only ensures that sealing of the mixing chamber occurs in the region around the membrane, but also effectively assists dispersion of the aerosol from the membrane into the mixing chamber. It is thereby advantageous that a reliable sealing at the surface of the aerosol generator can be ensured around the membrane by the aerosol passage. Furthermore, in the inhalation therapy device according to the invention, the breathing air is guided outside in relation to the aerosol passage, thereby protecting to a certain extent the aerosol entering into the mixing chamber via the aerosol passage such that an undesired impaction of aerosol particles or droplets on the wall of the mixing chamber is reduced.

A plurality of breathing air through openings are preferably provided, which are opened and closed by the one valve element or by several separate or connected valve elements.

A surrounding groove is provided for the simple retention of the valve element.

In order to reduce the risk of damage and to improve retention, the valve element comprises a bulge at the edge for retention in the surrounding groove.

In a preferred embodiment, the aerosol passage is pipe-shaped and the valve element is ring-shaped. The valve element then accommodates the pipe-shaped aerosol passage in the annular opening. In this case, the surrounding groove for accommodating the valve element is preferably provided in the outer surface of the pipe-shaped aerosol passage.

In a preferred embodiment, the pipe-shaped aerosol passage is formed by a cylindrical sleeve, disposed on the surface of which is a region accommodating the breathing air through openings, which extends essentially perpendicularly to the longitudinal axis of the sleeve. The sleeve is preferably disposed concentrically to the membrane. Adapting to this design, the valve element is configured in the shape of a circular ring and accommodates the cylindrical sleeve in the annular opening. The annular valve element correspondingly comprises a bulge at the edge of the annular opening for retention on the cylindrical sleeve. For fixation, the surrounding groove for accommodating the edge of the annular opening of the valve element is advantageously provided in the surface of the cylindrical sleeve.

In order to avoid damage and to assist sealing of the mixing chamber in the region of the membrane, the aerosol passage comprises a bulge in the region facing the surface of the aerosol membrane generator.

In a basic shape, the breathing air through openings extend essentially parallel to the aerosol passage. However, in an advantageous design, the breathing air through openings extend in a spiral manner in order to cause the air flowing in through the openings to swirl.

A design in which the breathing air through openings are formed as circular ring sections is basically preferred.

The inhalation valve is on the whole preferably designed with an edge section which is formed for retaining the inhalation valve, in particular for clamping between the aerosol generator and the mixing chamber.

The breathing air through openings are preferably designed to extend in a sloped manner such that the breathing air is guided away from the fixing point of the valve element. This thereby assists opening of the valve at the beginning of the inhalation phases and promotes an improved flow supply which leads to lower deposition rates, in particular on the mixing chamber walls.

Lower deposition rates are also achieved by a design in which the breathing air through openings are provided on all sides around the aerosol passage.

Figure 2:
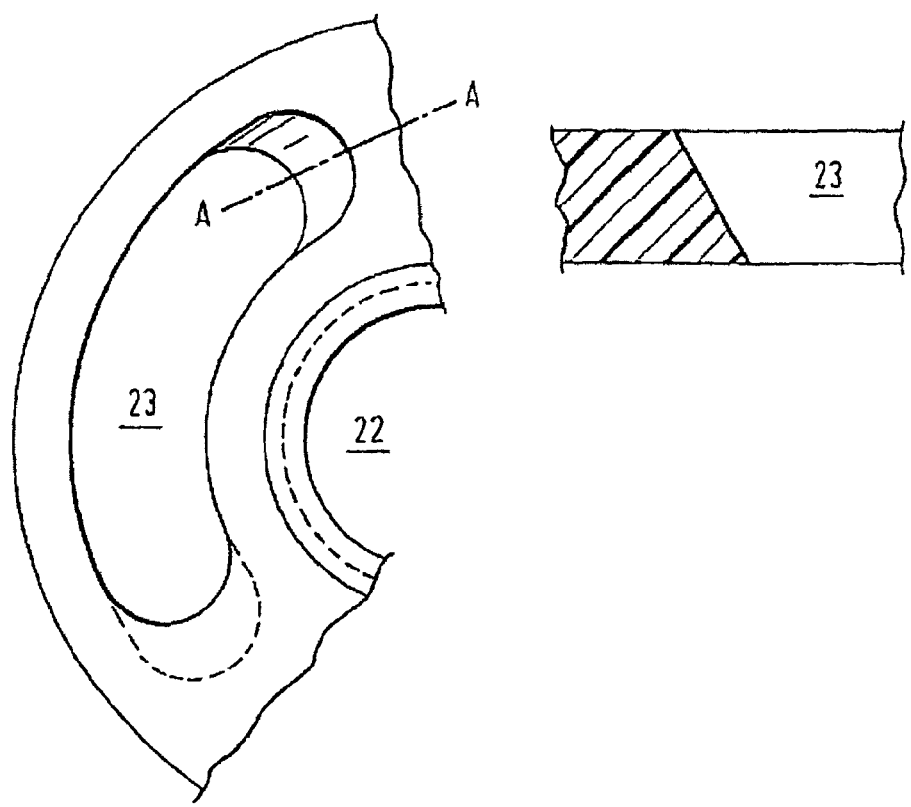

In a particular design, the region of the breathing air through openings is essentially disposed on a plane with the membrane.

The valve element is preferably produced from a resilient material. The inhalation valve is preferably also produced from a resilient material.

The invention is described in more detail in the following by means of an embodiment and referring to the figures.

FIG. 1 shows a cut view of an embodiment of an inhalation device according to the invention;

FIG. 2 shows a cut-out view of the region of the breathing air through openings with spirally configured openings;

FIGS. 3A and 3B show perspective views of an inhalation valve according to the invention;

FIG. 4 shows a further embodiment of an inhalation device according to the invention;

FIG. 5 shows a modification of the embodiment according to FIG. 4;

FIG. 6 shows a further embodiment of an inhalation device according to the invention;

FIG. 7 shows a modification of the embodiment according to FIG. 6; and

FIG. 8 shows a further embodiment of an inhalation device according to the invention.

FIG. 1 shows an embodiment of an inhalation therapy device 1 according to the invention, comprising an aerosol membrane generator 2 and a mixing chamber 3. In the shown embodiment, the two components are configured as separate units that are connected with one another in a suitable manner such that both components can be safely handled together as a functional unit.

The aerosol generator 2 of the embodiment according to FIG. 1 comprises a liquid storage container 4, into which a medicament-containing liquid 5 can be filled, and a membrane 6 which closes the liquid storage container 4 at an open surface. The membrane 6 is thereby connected on one side with the liquid container 4 such that the liquid 5 disposed in the liquid storage container contacts the one side of the membrane 6. An oscillation generator 7, for example a piezo element, is disposed on the membrane 6, by means of which the membrane 6 is caused to oscillate when the oscillation generator 7 is activated. In the embodiment shown here, the membrane 6 and the oscillation generator 7 are configured in a rotationally symmetrical manner such that the oscillation generator 7 concentrically surrounds the membrane.

If the oscillation generator 7 is activated, i.e., for example, an alternating voltage is supplied to the piezo element, the membrane 6 is caused to oscillate such that the liquid 5 that is disposed in the liquid storage container and abuts the membrane 6 is guided through openings in the membrane to the other side of said membrane 6 and is nebulised there into an aerosol. The aerosol is released into the mixing chamber 3.

The embodiment shown in FIG. 1 is furthermore provided with a mouthpiece 10 which is configured integrally with the mixing chamber 3 in the shown example, but which, however, can also be formed so as to be separable from the mixing chamber 3 in a modified embodiment. The patient inhales the aerosol that is generated by the aerosol membrane generator 2 and released into the mixing chamber 3 via the mouthpiece 10 when he breathes in through said mouthpiece.

During the inhalation phase, ambient air flows into the therapy device via air supply channels 8 that are formed in the aerosol membrane generator 2, and reaches the mixing chamber 3; the flow path of the supplied air is indicated in FIG. 1 by the dashed arrow lines 9. A valve element 21, which is described in more detail below, is thereby raised, which corresponds to the dashed position 21*a* in FIG. 1.

According to the invention, an inhalation valve 20 is provided to control the supplied air, which allows ambient air to flow into the mixing chamber during the inhalation phases but which, however, prevents exhaled air from reaching the aerosol membrane generator 2 from the mixing chamber in exhalation phases. The inhalation valve 20 according to the invention therefore prevents the aerosol being transported out of the mixing chamber with the exhaled air in exhalation phases and prevents exhaled air from flowing into the aerosol membrane generator 2. In the aerosol generator 2, the area around the liquid container 4, in which other components, for example electrical connections for activating the piezo crystal, can often also be found, is thereby protected from exhaled air and thus from impurities which could enter the therapy device with the exhaled air. The inhalation valve 20 according to the invention therefore protects the interior of the aerosol generator 2 during the exhalation phases by closing the mixing chamber 3 towards the aerosol membrane generator 2.

The exhaled air is guided out of the mixing chamber 3 or mouthpiece 10 in another manner, for example via a mouthpiece valve 33 known per se, which comprises a mouthpiece valve opening 321 and a mouthpiece valve element 322. However, the operating mode of the mouthpiece valve will not be described in more detail here.

According to the invention, the inhalation valve 20, as shown in FIG. 1, forms a wall section of the mixing chamber 3 by completing an open wall section of the mixing chamber 3 in a closing manner. In the embodiment shown in FIG. 1, the inhalation valve 20 is clamped between the aerosol membrane generator 2 and the mixing chamber 3.

The inhalation valve 20 comprises an aerosol passage 22 which allows the aerosol to arrive from the membrane into the mixing chamber. The inhalation valve 20 furthermore comprises one or more breathing air through openings 23, via which supplied air enters the mixing chamber in the inhalation phases and which are closed in the exhalation phases. The inhalation valve 20 comprises one or more valve elements 21 for this purpose. This basic construction is described as an example in more detail below by means of the embodiment according to FIG. 1.

In one embodiment, the inhalation valve 20 comprises a cylindrical sleeve which represents the aerosol passage via which the aerosol released from the membrane flows into the mixing chamber 3. The sleeve is aligned to the membrane 6 and is preferably disposed concentrically to said membrane 6. One end face of the sleeve rests on a surface of the membrane generator 2, which surrounds the membrane 6. The mixing chamber is thereby sealed in the area around the membrane 6, which prevents air exhaled during the exhalation phases from flowing past the membrane 6.

The aerosol passage 22 basically comprises an area for this purpose which is disposed on a surface of the aerosol membrane generator 2 such that the membrane is enclosed along at least one sealing line 20*a*. The aerosol passage 22 of the inhalation valve 20 ensures in this manner on the one hand that the aerosol can arrive from the membrane 6 into the mixing chamber 3 and that on the other hand a sealing of the mixing chamber 3 occurs in the region of the aerosol membrane generator 2.

As can be seen from FIG. 1, a region is provided in the shown embodiment around the sleeve 22 in which the breathing air through openings 23 are provided. The region containing the breathing air through openings extends essentially perpendicularly to the longitudinal axis of the sleeve 22. The breathing air through openings 23 are concentric to the cylindrical sleeve 22 and are formed in the shape of circular ring segments, of which one is shown in FIG. 2.

The embodiment of the breathing air through openings 23 shown in FIG. 2 is noteworthy in so much as the openings, deviating from a basic shape in which the breathing air through openings 23 extend basically parallel to the aerosol passage 22, are configured in a sloped manner such that a spiral-like design results. This configuration is illustrated in FIG. 2 by means of the cut along the line A-A. The spiral-like sloped design of the breathing air through openings 23 causes the breathing air flowing through these openings to swirl, which causes the breathing air to surround the aerosol flowing through the aerosol passage into the mixing chamber and to enclose it to a certain extent. The risk of impaction of the aerosol particles on the inner wall of the mixing chamber 3 is thereby further reduced.

A valve element 21 is disposed on the side of the region of the breathing air through openings 23 facing the mixing chamber, which has an annular shape and is flat in the shown embodiment and which accommodates the cylindrical sleeve in its central annular opening. In addition to the position in which the valve element 21 closes the breathing air through openings 23, FIG. 1 shows, as a dashed line, the valve element 21a in its raised position, i.e. during the inhalation phases.

In order to retain the valve element 21, the sleeve preferably comprises in the outer surface a surrounding groove 24 in which the inner edge of the annular opening of the valve element 21 is disposed. The edge of the annular opening is thereby provided with a bulge 26. This not only ensures a secure retention of the valve element 21 in the groove 24, but also protects the inner edge of the annular opening from damage during insertion.

In the embodiment shown in FIG. 1, the inhalation valve 20 is disposed between a wall section 31 of the aerosol generator 2 and a wall section 31 of the mixing chamber 3 and is preferably retained, for example clamped, such that the inhalation valve 20 is securely fixed and the aerosol passage 22 thereof is exactly positioned. The inhalation valve 20 comprises an external edge section 25 for this purpose, which is configured for retaining/fixing on the aerosol generator 2 and/or the mixing chamber 3. The embodiment shown in FIG. 1 is furthermore also particularly advantageous since the inhalation valve 20 is used for sealing the connection point between the aerosol generator 2 and the mixing chamber 3. The edge section 25 of the inhalation valve 20 is adapted for this purpose to the front face cross-sections of the aerosol generator 2 and the mixing chamber 3.

Figure 3A:
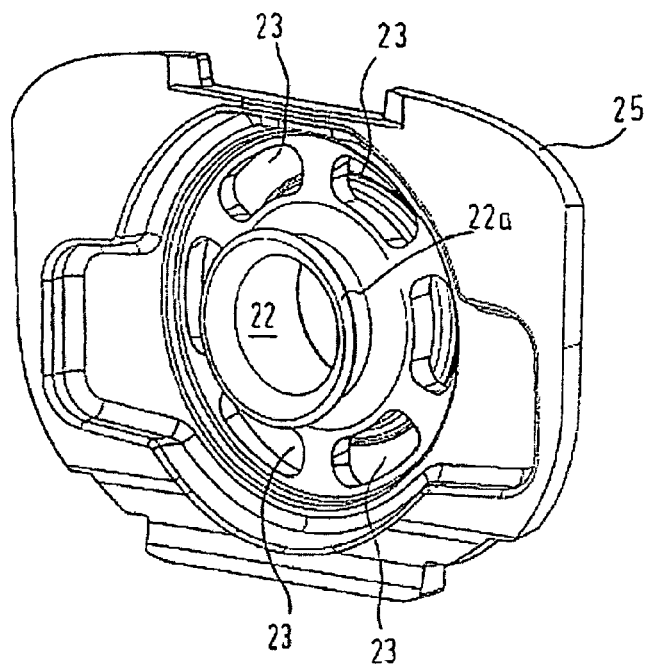
Figure 3B:
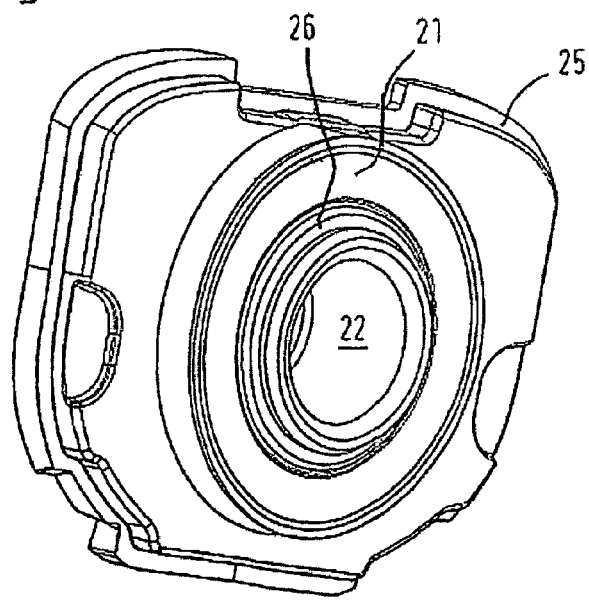

FIGS. 3A and 3B show that the adaptation of the edge section 25 to the cross-section of the membrane aerosol generator 2/mixing chamber 3 can be very extensive, however a transition to the region according to the invention having the breathing air through openings 23 can always be created in a problem-free manner. This type of adaptation achieves that the material of the inhalation valve 20 that is basically suitable for sealing purposes is also used for sealing the transition between the aerosol generator 2 and the mixing chamber 3.

It can furthermore be seen therefrom that the inhalation valve 20 according to the invention is preferably only configured from two parts. This is because one part comprises the sleeve, the region of the breathing air through openings 23, the transition region to the edge section 25 and the edge section 25 itself in one piece; the other part forms the valve element 21.

It can furthermore be seen from FIGS. 1 and 3A that the front face end of the cylindrical sleeve 22 facing the membrane preferably comprises a surrounding bulge 22a. The risk of damage to the front face end of the sleeve is thereby lowered. The bulge 26 on the inner edge of the annular opening of the valve element 21 can be clearly seen in FIG. 3B, which shows a perspective view of an inhalation valve according to the invention from the side of the mixing chamber 3.

FIG. 4 shows a further embodiment of an inhalation valve 20 according to the invention in a depiction in which parts of the aerosol membrane generator 2 and the mixing chamber 3 have not been shown; reference is made in this regard to FIG. 1. The storage container 4 and the liquid 5 which abuts the membrane 6 are recognisable in FIG. 4. The membrane 6 is provided in this embodiment with a dome section 6a, which curves outwards in the direction of the mixing chamber 3. A fixing section 6b of the membrane 6 helps to fix the membrane to a support 6c on which the oscillation generator 7, for example the piezo element, is attached. As regards the operating principle of the aerosol generator of this embodiment, reference is made to the statements made above in connection with FIG. 1.

The inventive inhalation valve 20 of this embodiment comprises an aerosol passage 22 which enables the aerosol released by the membrane to arrive in the mixing chamber 3. The aerosol passage 22 is basically a flat, funnel-shaped structure in this embodiment. The aerosol passage 22 comprises an area which lies on a surface of the aerosol membrane generator 2, according to FIG. 4 a surface of the oscillation generator 7, and surrounds the membrane 6 along a sealing line 20a. This area of the aerosol passage 22 is preferably equipped with a bulge 22a. It can be seen in the embodiment shown in FIG. 4 that the aerosol passage 22, the resulting sealing line 20a and the bulge 22a are preferably rotationally symmetrical.

As regards the aerosol passage 22, one or more breathing air through openings 23 are formed in a region provided therefor. These openings are covered by a valve element 21 in the direction of the mixing chamber 3 such that the openings are opened during the inhalation phases and are closed during the exhalation phases. The details of the valve element 21 correspond to those of the valve element of the embodiment described above, and thus reference can be made at this point to the explanations given above.

A projection 24a is provided on the aerosol passage 22 according to FIG. 4 for secure retention, which circular in the rotationally symmetrical design of the aerosol passage. The surrounding groove 24 is formed in this projection 24a, in which the valve element 21, preferably with the bulge 26, is fixed.

Furthermore, in the embodiment according to FIG. 4, an edge area 25 is attached to the area with the breathing air through openings 23, which is used for retaining the inhalation valve 20 in that the edge 25 is, for example, clamped between a wall 31 of the aerosol membrane generator 2 and a wall 32 of the mixing chamber 3.

FIG. 5 shows a modification of the embodiment according to FIG. 4 and reference is made to the description thereof also for FIG. 5. In order to clarify the modification, only those reference numbers are given in FIG. 5 which are directly related to the modification.

Deviating from the embodiment according to FIG. 4, the breathing air openings 23 are configured in the embodiment according to FIG. 5 such that they slope outwards. In other words, the breathing air through openings 23 extend away from the fixed point of the valve element 21 which is retained in the groove 24. The breathing air is thereby guided outwards in relation to the aerosol passage 22 and thus to the free end of the lifting section of the valve element 21, which leads to a more favourable flow into the mixing chamber 3 and to a lower trigger force for the valve element 21.

In addition to the sloping of the breathing air openings 23 shown in FIG. 5, a spiral design as described above in connection with FIG. 2 can also be provided in the embodiments according to FIGS. 4 and 5. In the design according to FIG. 5, the inhaled air is thereby not only guided outwards but is also additionally caused to swirl.

FIG. 6 shows a modification of the embodiment according to FIG. 4 and reference is made to the description thereof also for FIG. 6. In order to clarify the modification, only those reference numbers are given in FIG. 6 which are directly related to the modification.

Deviating from the embodiment according to FIG. 4, the projection 24a is disposed outwardly in relation to the aerosol passage 22, preferably in the vicinity of the edge area 25, in the embodiment according to FIG. 6. The surrounding groove 24 is configured in this projection 24a such that it opens towards the aerosol passage 22. The valve element 21 is accordingly retained at an outer edge in the groove 24 and advantageously comprises a bulge 26 on the outer edge for this purpose. The valve element 21 extends to the aerosol passage 22 with its flexible section and thereby covers the breathing air through openings 23. The operating mode of the valve element 21 of this embodiment otherwise fully corresponds to the embodiments described above.

Figure 7:
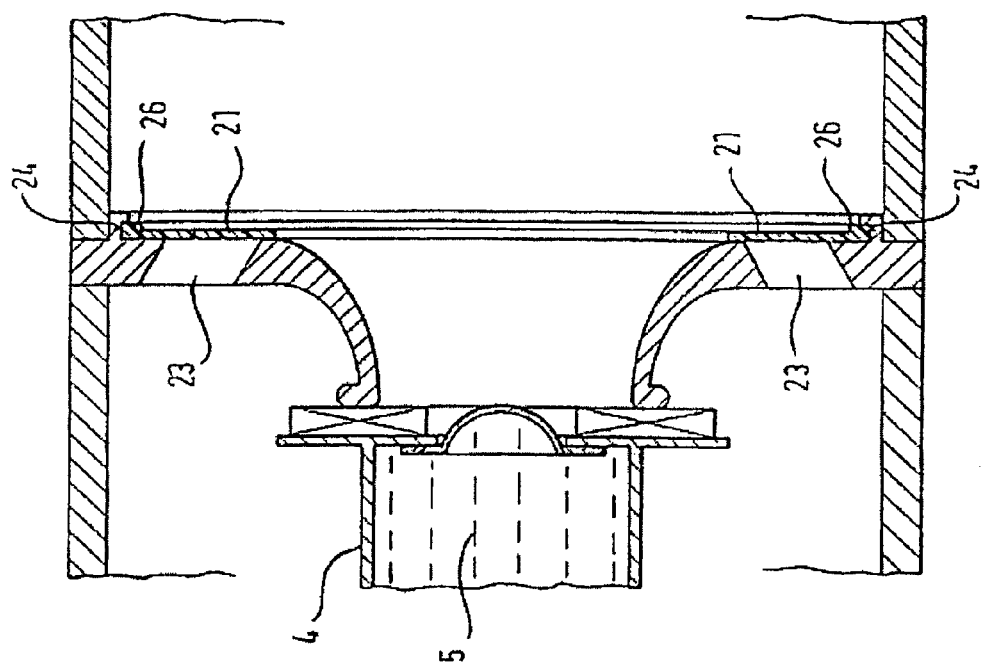

FIG. 7 shows a modification of the embodiment according to FIG. 6 and reference is made to the description thereof also for FIG. 7. In order to clarify the modification, only those reference numbers are given in FIG. 7 which are directly related to the modification.

Deviating from the embodiment according to FIG. 6, the breathing air openings 23 are configured in the embodiment according to FIG. 7 such that they slope inwardly. In other words, the breathing air through openings 23 extend away from the fixed point of the valve element 21 which is retained in the groove 24. The breathing air is thereby guided inwards in relation to the aerosol passage 22 and thus to the free end of the lifting section of the valve element 21, which leads to a more favourable flow into the mixing chamber 3 and to a lower trigger force for the valve element 21.

In addition to the sloping of the breathing air openings 23 shown in FIG. 7, a spiral-like design as described above in connection with FIG. 2 can also be provided in the embodiments according to FIGS. 6 and 7. In the design according to FIG. 7, the inhaled air is thereby not only guided inwards but is rather additionally caused to swirl.

Figure 8:
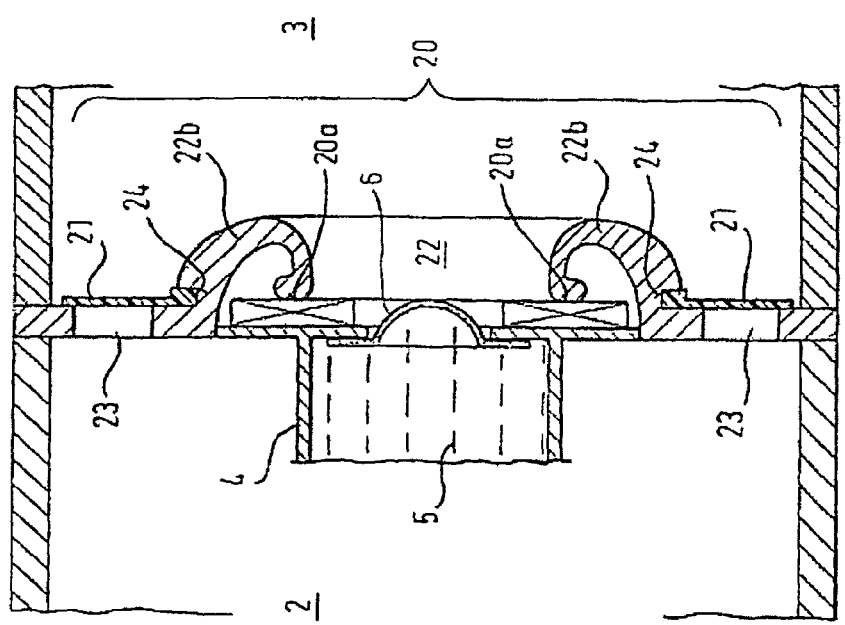

FIG. 8 shows a further embodiment of an inhalation valve 20 according to the invention in a depiction in which parts of the aerosol membrane generator 2 and the mixing chamber 3 have not been shown; reference is made in this regard to FIG. 1. In this embodiment, the aerosol passage 22 is configured in a very flat manner; the region with the breathing air through openings 23 is essentially disposed on a plane with the membrane 6 of the aerosol membrane generator 2. However, the aerosol passage 22 of this inhalation valve 20 also comprises, in accordance with the invention, a region which lies on a surface of the aerosol membrane generator 2 and which surrounds the membrane along at least one sealing line 20a, whereby ensuring sealing of the mixing chamber around the membrane. According to the invention, the valve element 21 is configured and disposed such that it closes the breathing air through openings 23 during the exhalation phases and opens them during the inhalation phases. A transition area 22b is formed between the aerosol passage 22 and the region of the breathing air through openings 23, in which the surrounding groove 24 is preferably provided. In accordance with FIG. 6 or 7, a projection accommodating the groove can, however, also be provided outside. In this embodiment, the breathing air through openings 23 can also, in accordance with FIGS. 5 and 7, extend outwardly or inwardly in a sloping manner relative to the fixing point of the valve element 21 and can be configured in a spiral manner in accordance with FIG. 2.

The invention claimed is:

1. An inhalation therapy device comprising
a) an aerosol membrane generator having:
   i) a liquid storage container, into which a medicament-containing liquid that can be used for therapy is fillable,
   ii) a membrane closing said liquid storage container at an open surface of the liquid storage container such that said medicament-containing liquid disposed in the liquid storage container always contacts a backside of said membrane, and
   iii) an oscillation generator for generating oscillations by which said liquid disposed in the liquid storage container is nebulised into an aerosol through openings in the membrane to the other side of said membrane,
b) a mixing chamber into which the aerosol membrane generator generates the aerosol, and
c) an inhalation valve which allows the inflow of ambient air via a flow path directly from outside the inhalation therapy device via at least one breathing air through opening into the mixing chamber during inhalation phases, which prevents the aerosol from escaping from the mixing chamber during exhalation phases and which forms a wall section of said mixing chamber, the inhalation valve having
   i) an aerosol passage, via which the aerosol generated by the membrane generator arrives in the mixing chamber, said aerosol passage being disposed with one section on a surface of the aerosol membrane generator so as to surround the membrane along at least one sealing line, and extending in an opening manner into the mixing chamber,
   ii) said at least one breathing air through opening disposed in a region around the aerosol passage, and
   iii) a valve element disposed in the region around the aerosol passage such that the valve element closes the at least one breathing air through opening in exhalation phases and opens the at least one breathing air through opening in inhalation phases;
   wherein the at least one breathing air through opening extends substantially parallel to the aerosol passage; and
   wherein the inhalation valve is positioned in a cross-section of the inhalation therapy device in a plane with the membrane or in front of the membrane toward the mixing chamber.

2. The inhalation therapy device of claim 1, wherein a plurality of breathing air through openings are provided.

3. The inhalation therapy device of claim 1, wherein a surrounding groove is provided to retain the valve element.

4. The inhalation therapy device of claim 3, wherein the valve element comprises a bulge for retention in the surrounding groove.

5. The inhalation therapy device of claim 1, wherein the aerosol passage is pipe-shaped and the valve element is annular and said valve element accommodates the pipe-shaped aerosol passage in an annular opening.

6. The inhalation therapy device of claim 5, wherein a surrounding groove is provided to accommodate the valve element in an outer surface of the pipe-shaped aerosol passage.

7. The inhalation therapy device of claim 5, wherein the pipe-shaped aerosol passage is formed by a cylindrical sleeve, provided on an outer surface of which is a region accommodating the at least one breathing air through opening, which extends essentially perpendicular to the longitudinal axis of the sleeve.

8. The inhalation therapy device of claim 7, wherein the cylindrical sleeve is disposed concentrically to the membrane.

9. The inhalation therapy device of claim 7, wherein the valve element is configured as a circular ring and accommodates the cylindrical sleeve in the annular opening.

10. The inhalation therapy device of claim 1, wherein the aerosol passage comprises a bulge in an area facing the membrane.

11. The inhalation therapy device of claim 1, wherein the one or more breathing air through openings extend relative to the aerosol passage to cause breathing air flowing through the through openings to swirl.

12. The inhalation therapy device of claim 1, wherein the one or more breathing air through openings are configured as circular ring sections or segments.

13. The inhalation therapy device of claim 1, wherein the one or more breathing air through openings are disposed around a periphery of the aerosol passage.

14. The inhalation therapy device of claim 1, wherein the at least one breathing air through opening is designed to extend in a sloping manner such that breathing air is guided away from a fixing point of the valve element.

15. The inhalation therapy device claim 1, wherein the region of the one or more breathing air through openings is disposed essentially on a plane with the membrane.

16. The inhalation therapy device of claim 1, wherein the valve element is produced from a resilient material.

17. The inhalation therapy device of claim 1, wherein the inhalation valve is produced from a resilient material.

* * * * *